United States Patent [19]
O'Lenick, Jr.

[11] Patent Number: 5,917,070
[45] Date of Patent: Jun. 29, 1999

[54] POLYOXYALKYLENE GLYCOL MEADOWFOAM ESTERS

[75] Inventor: Anthony J. O'Lenick, Jr., Lilburn, Ga.

[73] Assignee: Fan Tech Ltd., Chicago, Ill.

[21] Appl. No.: 08/773,734

[22] Filed: Dec. 26, 1996

Related U.S. Application Data

[63] Continuation-in-part of application No. 08/516,138, Aug. 17, 1995, Pat. No. 5,646,321.

[51] Int. Cl.$^6$ .................................................. C07C 57/00
[52] U.S. Cl. ........................... 554/224; 554/223; 554/227
[58] Field of Search ................................... 554/224, 223, 554/227

[56] References Cited

U.S. PATENT DOCUMENTS

| | | |
|---|---|---|
| 4,425,458 | 1/1984 | Lindner et al. . |
| 4,868,236 | 9/1989 | O'Lenick . |

OTHER PUBLICATIONS

Morrison & Boyd, Organic Chemistry, 4th ed., p. 828, 1983.

*Primary Examiner*—Gary Geist
*Assistant Examiner*—Deborah D. Carr

[57] ABSTRACT

The present invention deals with the composition of matter and the utilization of certain novel polyoxyalkylene glycol esters which are prepared by the reaction of a meadowfoam oil, meadowfoam fatty acid or meadowfoam methyl ester and a polyoxylalkylene glycol as emulsifiers.

14 Claims, No Drawings

POLYOXYALKYLENE GLYCOL MEADOWFOAM ESTERS

RELATED APPLICATIONS

This application is a continuation in part of Ser. No. 516,138 filed Aug. 17, 1995, now U.S. Pat. 5,646,321.

BACKGROUND OF THE INVENTION

1. Field of the Invention

The present invention deals with novel emulsifiers. The compounds are polyoxyalkylene glycol esters of meadowfoam oil, meadowfoam acid or meadowfoam methylester. The introduction of the meadowfoam portion of the molecule into the compounds of the present invention results in improved emulsification efficiency and improved liquidity of the esters.

2. Description of the Art Practices

Polyoxyalkylene glycol esters based upon linear, saturated compounds are known in the art. Variation of carbon chain lengths in the fatty source has direct effect upon the emulsification properties. While short chain fatty materials result in compounds which are not good emulsifiers, incorporation of fatty groups having more that 12 carbon atoms result in emulsifiers. They are however solids with relatively high melting points.

The use of higher molecular weight unsaturated fatty acids to prepare esters results in products which suffer from oxidative instability and interfere with the fragrance of many products.

The recent availability of meadowfoam oil, with it's 20 to 22 carbon atoms and the specific location of it's double bonds, and it's reaction to make esters results in the preparation liquid stable esters, having outstanding emulsifing properties and are very acceptable for use in personal care applications.

None of the prior amides possess the critical meadowfoam carboxy moiety. Molecules of the current invention have the meadowfoam alkyl group in the ester.

THE INVENTION

This invention relates to the use of meadowfoam oil, weather as the triglyceride, acid or methyl ester and it's reaction with polyoxyalkylene glycol compounds to prepare a polyoxyalkylene glycol esters.

Esters are a class of compounds which find applications in many diverse segments of the chemical industry. One of the problems which is encountered using saturated fatty acids to make polyoxyalkylene glycol esters is the fact that these materials are waxy solids with relatively high melting points. They possess some desirable surfactant properties, like emulsification, but need to be used in relatively high concentrations. It is very desirable to limit the concentration of surfactant in making emulsions. The emulsifiers used in a water in oil emulsion for example allows for the preparation of emulsion, but the delivery of the oil from the emulsion can be limited by a high level of emulsifier.

The specific structure of the ester determines the functional attributes of the product, including emulsification and liquidity. There are many possible structural variations which can impact upon the performance of esters. We have learned that the presence of a specific carbon distribution in the acid side of the molecule results in improved properties.

The unique structure of the oil coupled with the proper selection of the meadowfoam chosen to make the ester results in a liquid ester with oxidative stability heretofore unattainable. The fatty distribution of the oil ranges from 20 to 22 carbons and has unsaturation in specific locations. The oil contains 97% by weight higher unsaturated alkyl groups. Typically, meadowfoam oil contains 60–65% of a twenty carbon mono-carboxy acid having one unsaturation between carbon 5 and 6. Additionally, it contains 12–20% of a twenty two carbon mono-carboxy acid having one unsaturation between either carbon 5 and 6, or carbon 13 and 14 and 15–28 % of a twenty two carbon mono-carboxy acid having one unsaturation between both carbon 5 and 6, or carbon 13 and 14. The combination of the fact that there are 20 to 22 carbon atoms in the group leads to lack of volatility, the presence of unsaturation leads to liquidity and the fact that the di-unsaturated moieties are not conjugated leads to outstanding oxidative stability.

Additional aspects of the invention is the application of these materials as personal care applications were the specific properties of the ester having the unique distribution of the meadowfoam on the other result in superior liquidity, lubricity, and outstanding oxidative stability.

The compounds of the current invention are polyoxyalkylene gylcol esters derived from meadowfoam conforming to the following structure;

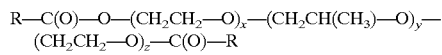

wherein:

R is derived from meadowfoam and is;
60–65% by weight

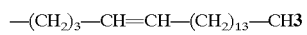

12–20% by weight a mixture of

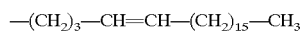

and

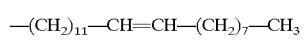

and
15–28% by weight

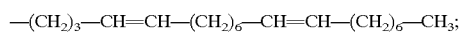

x, y and z are independently integers ranging from 0 to 115, with the proviso that x+y+z be greater than 1.

The ester is prepared by the esterification reaction as shown below:

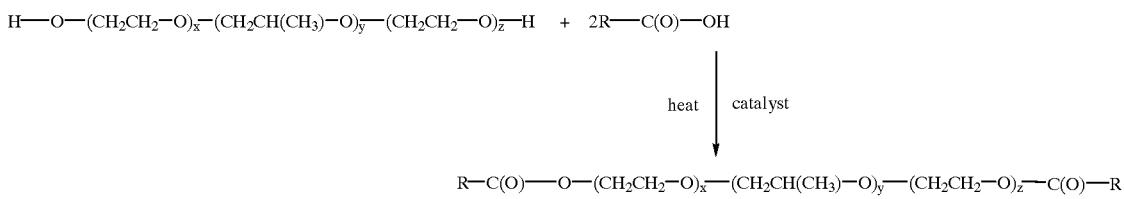

R is derived from meadowfoam;

x, y and z are independently intergers ranging from 0 to 115, with the proviso that x+y+z be greater than 1.

EXAMPLES

Raw Materials

Meadowfoam Oil

Meadowfoam Oil can be used as a triglyceride, which is the oil as provided, reacted with methanol in processes known to those skilled in the art to make methyl ester, or reacted using technology known in the art to make carboxylic acids. The CAS number of meadowfoam oil is 153065-40-8.

The choice of triglyceride, acid or methyl ester does not change the structure of the resultant ester. It does however change the by-product produced. In the case of the triglyceride, glycerine is produced, in the case of the acid water is produced and in the case of the methyl ester methanol is produced.

Polyoxyalkylene Glycol Compounds

The compounds conform to the following structure:

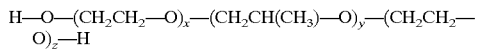

x, y and z are independently integers ranging from 0 to 115, with the proviso that x+y+z be greater than 1. wherein:

| Example | x | y | z |
|---------|-----|-----|-----|
| 1 | 14 | 0 | 0 |
| 2 | 23 | 0 | 0 |
| 3 | 9 | 0 | 0 |
| 4 | 4 | 0 | 0 |
| 5 | 1 | 0 | 0 |
| 6 | 115 | 0 | 0 |
| 7 | 0 | 1 | 0 |
| 8 | 0 | 17 | 0 |
| 9 | 0 | 115 | 0 |
| 10 | 0 | 1 | 0 |
| 11 | 10 | 10 | 115 |
| 12 | 1 | 1 | 1 |
| 13 | 50 | 10 | 10 |

General Procedure—Meadowfoam Oil

To the specified number of grams the specified polyoxyalkylene glycol (Examples 1–13) is added 354.0 grams of meadofoam oil. Next add 0.1% stannous oxylate based upon the total weight of the batch after all ingredients have been charged, under agitation. The temperature of the mass is raised to 180–200C. and water is stripped off as formed. The saponification value increases to theoretical.

The products are clear liquids and are liquid to extraordinary temperatures. They exhibit outstanding lubrication properties and are outstanding viscosity index modifiers.

Example 14

To 616.0 grams of the specified polyoxyalkylene glycol (Examples 1) is added 354.0 grams of meadowfoam oil. Next add 0.1% stannous oxylate based upon the total weight of the batch after all ingredients have been charged, under agitation. The temperature of the mass is raised to 180–200 C. and water is stripped off as formed. The saponification value increases to theoretical.

Example 15–28

Example 14 is repeated, only this time the specified amount of the specified polyoxyalkylene glycol is substituted for the polyoxyalkylene glycol example 1.

|  | Polyoxyalkylene Glycol | |
|---------|---------|--------|
| Example | Example | Grams |
| 15 | 8 | 308.0 |
| 16 | 9 | 506.0 |
| 17 | 10 | 198.0 |
| 18 | 11 | 88.0 |
| 19 | 12 | 22.0 |
| 20 | 13 | 2500.0 |
| 21 | 14 | 30.0 |
| 22 | 15 | 501.0 |
| 23 | 16 | 3393.0 |
| 24 | 17 | 51.2 |
| 25 | 18 | 3106.0 |
| 26 | 19 | 73.5 |
| 27 | 20 | 2795.0 |
| 28 | 20 | 2795.0 |

General Procedure—Meadowfoam Fatty Acid

To the specified number of grams the specified polyoxyalkylene glycol (Examples 1–13) is added 354.0 grams of meadofoam fatty acid. Next add 0.1% stannous oxylate based upon the total weight of the batch after all ingredients have been charged, under agitation. The temperature of the mass is raised to 180–200 C. and water is stripped off as formed. The acid value and hydroxyl value drop to vanishingly small values, and the saponification value increases to theoretical.

The products are clear liquids and are liquid to extraordinary temperatures. They exhibit outstanding lubrication properties and are outstanding viscosity index modifiers.

Example 29

To 616.0 grams of polyoxyalkylene glycol (Examples 1) is added 354.0 grams of meadowfoam fatty acid. Next add 0.1% stannous oxylate based upon the total weight of the batch after all ingredients have been charged, under agitation. The temperature of the mass is raised to 180–200 C. and water is stripped off as formed. The acid value and hydroxyl value drop up to vanishingly small values, and the saponification value increases to theoretical.

Example 29–43

Example 29 is repeated, only this time the specified amount of the specified polyoxyalkylene glycol is substituted for the polyoxyalkylene glycol example 1.

| | Polyoxyalkylene Glycol | |
|---|---|---|
| Example | Example | Grams |
| 30 | 8 | 308.0 |
| 31 | 9 | 506.0 |
| 32 | 10 | 198.0 |
| 33 | 11 | 88.0 |
| 34 | 12 | 22.0 |
| 35 | 13 | 2500.0 |
| 36 | 14 | 30.0 |
| 37 | 15 | 501.0 |
| 38 | 16 | 3393.0 |
| 39 | 17 | 51.2 |
| 40 | 18 | 3106.0 |
| 41 | 19 | 73.5 |
| 42 | 20 | 2795.0 |
| 43 | 20 | 2795.0 |

The compound of the present invention are liquid esters with outstanding emulsification properties.

I claim:

1. A compound which conforms to the following structure:

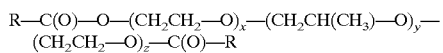
$$R-C(O)-O-(CH_2CH_2-O)_x-(CH_2CH(CH_3)-O)_y-(CH_2CH_2-O)_z-C(O)-R$$

wherein:

R is derived from meadowfoam and is:

60–65% by weight

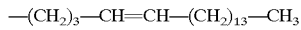
$$-(CH_2)_3-CH=CH-(CH_2)_{13}-CH_3$$

12–20% by weight a mixture of

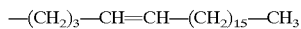
$$-(CH_2)_3-CH=CH-(CH_2)_{15}-CH_3$$

and $$-(CH_2)_{11}-CH=CH-(CH_2)_7-CH_3;$$

and

15–28% by weight $$-(CH_2)_3-CH=CH-(CH_2)_6-CH=CH-(CH_2)_6-CH_3;$$

x, y and z are independently integers ranging from 0 to 115, with the proviso that x+y+z be greater than 1.

2. A compound of claim 1 wherein.

x is 14, y is 0 and z is 0.

3. A compound of claim 1 wherein:

x is 23, y is 0, and z is 0.

4. A compound of claim 1 wherein:

X is 9, y is 0 and z is 0.

5. A compound of claim 1 wherein:

x is 4, y is 0 and z is 0.

6. A compound of claim 1 wherein:

x is 0, y is 0, and z is 0.

7. A compound of claim 1 wherein:

x is 115, y is 0 and z is 0.

8. A compound of claim 1 wherein:

x is 0, y is 1, z is 0.

9. A compound of claim 1 wherein:

is 0, y is 17 and z is 0.

10. A compound of claim 1 wherein:

X is 0, y is 115, and z is 0.

11. A compound of claim 1 wherein:

x is 0, y is 1, and z is 0.

12. A compound of claim 1 wherein:

x is 10, y is 10, and z is 115.

13. A compound of claim 1 wherein:

x is 1, y is 1, and z is 1.

14. A compound of claim 1 wherein:

x is 50 , y is 10 , z is 10.

* * * * *